United States Patent
Hetke et al.

(10) Patent No.: US 11,690,548 B2
(45) Date of Patent: *Jul. 4, 2023

(54) METHOD FOR IMPLANTING AN IMPLANTABLE DEVICE IN BODY TISSUE

(71) Applicant: NeuroNexus Technologies, Inc., Ann Arbor, MI (US)

(72) Inventors: Jamille Farraye Hetke, Brooklyn, MI (US); Daryl R. Kipke, Dexter, MI (US); Rio J. Vetter, Van Buren Township, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 1284 days.

This patent is subject to a terminal disclaimer.

(21) Appl. No.: 16/048,948

(22) Filed: Jul. 30, 2018

(65) Prior Publication Data

US 2019/0021618 A1 Jan. 24, 2019

Related U.S. Application Data

(63) Continuation of application No. 14/623,747, filed on Feb. 17, 2015, now Pat. No. 10,034,615, which is a
(Continued)

(51) Int. Cl.
*A61B 5/24* (2021.01)
*A61B 5/00* (2006.01)
(Continued)

(52) U.S. Cl.
CPC .............. *A61B 5/24* (2021.01); *A61B 5/4041* (2013.01); *A61B 5/6877* (2013.01); *A61N 1/05* (2013.01);
(Continued)

(58) Field of Classification Search
CPC ........ A61B 5/6877; A61B 2017/00004; A61B 2562/046; A61B 2562/164; A61N 1/0551
See application file for complete search history.

(56) References Cited

U.S. PATENT DOCUMENTS 3,752,939 A  8/1973  Bartz
3,847,687 A  11/1974 Davidsohn et al.
(Continued)

FOREIGN PATENT DOCUMENTS

AU  5172085  7/1986
AU  7322787  9/1987
(Continued)

OTHER PUBLICATIONS

Bouaziz, A. et al., "Vascular endothelial cell responses to different electrically charged poly((vinylidene fluoride) supports under static and oscillating flow conditions," Biomaterials vol. 18, No. 2, Jan. 1997 (Jan. 1997), pp. 107-112.
(Continued)

*Primary Examiner* — Joseph M Dietrich
(74) *Attorney, Agent, or Firm* — Haynes and Boone, LLP

(57) ABSTRACT

An implantable device for body tissue, including an electrical subsystem that flexes within and interfaces with body tissue and a carrier that operates in the following two modes: provides structural support for the electrical subsystem during implantation of the device in body tissue and allows flexing of the electrical subsystem after implantation of the device in body tissue. The implantable device is preferably designed to be implanted into the brain, spinal cord, peripheral nerve, muscle, or any other suitable anatomical location. The implantable device, however, may be alternatively used in any suitable environment and for any suitable reason.

20 Claims, 3 Drawing Sheets

Related U.S. Application Data continuation of application No. 12/253,813, filed on Oct. 17, 2008, now Pat. No. 8,958,862.

(60) Provisional application No. 60/980,659, filed on Oct. 17, 2007.

(51) Int. Cl.
*A61N 1/05* (2006.01)
*A61B 17/00* (2006.01)

(52) U.S. Cl.
CPC .. *A61N 1/0551* (2013.01); *A61B 2017/00004* (2013.01); *A61B 2562/028* (2013.01); *A61B 2562/046* (2013.01); *A61B 2562/164* (2013.01)

(56) References Cited

U.S. PATENT DOCUMENTS

| | | | |
|---|---|---|---|
| 3,921,916 | A | 11/1975 | Bassous |
| 4,141,365 | A | 2/1979 | Fischell et al. |
| 4,166,469 | A | 9/1979 | Littleford |
| 4,284,085 | A | 8/1981 | Hansen et al. |
| 4,306,562 | A | 12/1981 | Osborne |
| 4,357,497 | A | 11/1982 | Hochmair et al. |
| 4,455,192 | A | 6/1984 | Tamai |
| 4,461,304 | A | 7/1984 | Kuperstein |
| 4,465,482 | A | 8/1984 | Tittle |
| 4,541,440 | A | 9/1985 | Parsonnet |
| 4,686,765 | A | 8/1987 | Byers et al. |
| 4,762,135 | A | 8/1988 | van der Puije |
| 4,819,647 | A | 4/1989 | Byers et al. |
| 4,886,065 | A | 12/1989 | Collins, Jr. |
| 4,904,237 | A | 2/1990 | Janese |
| 4,961,434 | A | 10/1990 | Stypulkowski |
| 4,969,468 | A | 11/1990 | Byers et al. |
| 5,108,819 | A | 4/1992 | Heller et al. |
| 5,123,422 | A | 6/1992 | Charvin |
| 5,180,376 | A | 1/1993 | Fischell et al. |
| 5,207,709 | A | 5/1993 | Picha |
| 5,215,088 | A | 6/1993 | Normann et al. |
| 5,263,977 | A | 11/1993 | Adams et al. |
| 5,308,442 | A | 5/1994 | Taub et al. |
| 5,322,064 | A | 6/1994 | Lundquist |
| 5,385,635 | A | 1/1995 | O'Neill |
| 5,390,671 | A | 2/1995 | Lord et al. |
| 5,409,469 | A | 4/1995 | Schaerf |
| 5,496,360 | A | 3/1996 | Hoffmann et al. |
| 5,515,848 | A | 5/1996 | Corbett, III et al. |
| 5,524,338 | A | 6/1996 | Martyniuk et al. |
| 5,531,780 | A | 7/1996 | Vachon |
| 5,573,520 | A | 11/1996 | Schwartz et al. |
| 5,585,827 | A | 12/1996 | Murakami |
| 5,588,597 | A | 12/1996 | Reinecke et al. |
| 5,653,742 | A | 8/1997 | Parker et al. |
| 5,716,391 | A | 2/1998 | Grandjean |
| 5,720,099 | A | 2/1998 | Parker et al. |
| 5,744,958 | A | 4/1998 | Werne |
| 5,800,535 | A | 9/1998 | Howard, III |
| 5,843,148 | A | 12/1998 | Gijsbers |
| 5,843,150 | A | 12/1998 | Dreessen et al. |
| 5,897,583 | A | 4/1999 | Meyer et al. |
| 5,927,277 | A | 7/1999 | Baudino et al. |
| 5,928,458 | A | 7/1999 | Aschenbrenner et al. |
| 5,938,694 | A | 8/1999 | Jaraczewski et al. |
| 5,975,085 | A | 11/1999 | Rise et al. |
| 5,992,769 | A | 11/1999 | Wise et al. |
| 6,006,124 | A | 12/1999 | Fischell et al. |
| 6,016,449 | A | 1/2000 | Fischell et al. |
| 6,044,304 | A | 3/2000 | Baudino et al. |
| 6,061,593 | A | 5/2000 | Fischell et al. |
| 6,078,841 | A | 6/2000 | Kuzma |
| 6,091,979 | A | 7/2000 | Madsen |
| 6,119,044 | A | 9/2000 | Kuzma |
| 6,128,521 | A | 10/2000 | Marro et al. |
| 6,132,456 | A | 10/2000 | Sommer et al. |
| 6,181,569 | B1 | 1/2001 | Chakravorty |
| 6,205,361 | B1 | 3/2001 | Kuzma et al. |
| 6,228,111 | B1 | 5/2001 | Tormala et al. |
| 6,296,630 | B1 | 10/2001 | Altman et al. |
| 6,324,433 | B1 | 11/2001 | Errico |
| 6,325,797 | B1 | 12/2001 | Stewart et al. |
| 6,374,143 | B1 | 4/2002 | Berrang et al. |
| 6,430,443 | B1 | 8/2002 | Karell |
| 6,600,231 | B2 | 7/2003 | Tominaga |
| 6,611,715 | B1 | 8/2003 | Boveja |
| 6,618,623 | B1 | 9/2003 | Pless et al. |
| 6,829,498 | B2 | 12/2004 | Kipke et al. |
| 6,834,200 | B2 | 12/2004 | Moxon et al. |
| 6,878,643 | B2 | 4/2005 | Krulevitch et al. |
| 7,004,948 | B1 | 2/2006 | Pianca et al. |
| 7,006,859 | B1 | 2/2006 | Osorio et al. |
| 7,010,356 | B2 | 3/2006 | Jog et al. |
| 7,011,680 | B2 | 3/2006 | Alt |
| 7,089,059 | B1 | 8/2006 | Pless |
| 7,181,288 | B1 | 2/2007 | Rezai et al. |
| 7,343,205 | B1 | 3/2008 | Pianca et al. |
| 7,548,775 | B2 | 6/2009 | Kipke et al. |
| 7,871,707 | B2 | 1/2011 | Laude et al. |
| 7,914,842 | B1 | 3/2011 | Greenberg et al. |
| 7,941,202 | B2 | 5/2011 | Hetke et al. |
| 8,731,673 | B2 | 5/2014 | Vetter et al. |
| 8,800,140 | B2 | 8/2014 | Hetke et al. |
| 8,958,862 | B2 | 2/2015 | Hetke et al. |
| 10,034,615 | B2 | 7/2018 | Hetke et al. |
| 2001/0049499 | A1 | 12/2001 | Lui et al. |
| 2002/0052610 | A1 | 5/2002 | Skakoon et al. |
| 2002/0183817 | A1 | 12/2002 | Van Venrooij et al. |
| 2002/0198446 | A1 | 12/2002 | Hill et al. |
| 2003/0093104 | A1 | 5/2003 | Bonner et al. |
| 2003/0093129 | A1 | 5/2003 | Nicolelis et al. |
| 2003/0100823 | A1 | 5/2003 | Kipke |
| 2003/0114906 | A1 | 6/2003 | Booker et al. |
| 2003/0187461 | A1 | 10/2003 | Chin |
| 2004/0006264 | A1 | 1/2004 | Mojarradi et al. |
| 2004/0102828 | A1 | 5/2004 | Lowry et al. |
| 2004/0106169 | A1 | 6/2004 | Evans |
| 2004/0122501 | A1 | 6/2004 | Dadd et al. |
| 2004/0199235 | A1 | 10/2004 | Younis |
| 2005/0004627 | A1 | 1/2005 | Gibson et al. |
| 2005/0021116 | A1 | 1/2005 | He et al. |
| 2005/0021117 | A1 | 1/2005 | He et al. |
| 2005/0075684 | A1 | 4/2005 | Phillips et al. |
| 2005/0118236 | A1 | 6/2005 | Qiu et al. |
| 2005/0137647 | A1 | 6/2005 | Wallace et al. |
| 2005/0222647 | A1 | 10/2005 | Wahlstrand et al. |
| 2006/0122677 | A1 | 6/2006 | Vardiman |
| 2006/0173263 | A1 | 8/2006 | He et al. |
| 2006/0247749 | A1 | 11/2006 | Colvin |
| 2006/0258951 | A1 | 11/2006 | Bleich et al. |
| 2006/0276866 | A1 | 12/2006 | McCreery |
| 2006/0282014 | A1 | 12/2006 | Kipke et al. |
| 2007/0073130 | A1 | 3/2007 | Finch et al. |
| 2007/0123765 | A1 | 5/2007 | Hetke et al. |
| 2007/0135885 | A1 | 6/2007 | Risi |
| 2008/0132970 | A1 | 6/2008 | Barolat |
| 2008/0208283 | A1 | 8/2008 | Vetter et al. |
| 2008/0255439 | A1 | 10/2008 | Tang et al. |
| 2008/0262584 | A1 | 10/2008 | Bottomley et al. |
| 2009/0052423 | A1 | 2/2009 | Aghvami et al. |
| 2009/0099441 | A1 | 4/2009 | Giszter et al. |
| 2009/0099555 | A1 | 4/2009 | Viohl et al. |
| 2009/0102068 | A1 | 4/2009 | Pellinen et al. |
| 2009/0118806 | A1 | 5/2009 | Vetter et al. |
| 2009/0132042 | A1 | 5/2009 | Hetke et al. |
| 2009/0149934 | A1 | 6/2009 | Ameri et al. |
| 2009/0171421 | A1 | 7/2009 | Atalar et al. |
| 2009/0187196 | A1 | 7/2009 | Vetter et al. |
| 2009/0234426 | A1 | 9/2009 | Pellinen et al. |
| 2009/0240314 | A1 | 9/2009 | Kong et al. |
| 2009/0248118 | A1 | 10/2009 | Bradley et al. |
| 2009/0253977 | A1 | 10/2009 | Kipke et al. |
| 2009/0299167 | A1 | 12/2009 | Seymour |
| 2009/0312770 | A1 | 12/2009 | Kozai et al. |
| 2010/0030298 | A1 | 2/2010 | Martens et al. |

(56) References Cited

U.S. PATENT DOCUMENTS

| | | |
|---|---|---|
| 2010/0145216 A1 | 6/2010 | He et al. |
| 2010/0145422 A1 | 6/2010 | Seymour et al. |
| 2011/0093052 A1 | 4/2011 | Anderson et al. |
| 2011/0154655 A1 | 6/2011 | Hetke et al. |
| 2015/0157854 A1 | 6/2015 | Hetke et al. |

FOREIGN PATENT DOCUMENTS

| | | |
|---|---|---|
| DE | 10032000 | 1/2001 |
| EP | 0002068 | 5/1979 |
| EP | 1602393 | 12/2005 |
| EP | 1723983 | 11/2006 |
| WO | WO1998707511 | 12/1987 |
| WO | WO0199300439 | 1/1993 |
| WO | WO1994000088 | 1/1994 |
| WO | WO1995026714 | 10/1995 |
| WO | WO1987030670 | 8/1997 |
| WO | WO1997039795 | 10/1997 |
| WO | WO1999949934 | 10/1999 |
| WO | WO1999055360 | 11/1999 |
| WO | WO2001012115 | 2/2001 |
| WO | WO2001097906 A2 | 12/2001 |
| WO | WO2001097906 A3 | 12/2001 |
| WO | WO2002036002 | 5/2002 |
| WO | WO2002041666 | 5/2002 |
| WO | WO2002045795 A2 | 6/2002 |
| WO | WO2002045795 A3 | 6/2002 |
| WO | WO2002096482 A2 | 12/2002 |
| WO | WO2002096482 A3 | 12/2002 |
| WO | WO2003028521 A2 | 4/2003 |
| WO | WO2003028521 A3 | 4/2003 |
| WO | WO2005039696 | 5/2005 |
| WO | WO2006/055593 A2 | 5/2006 |
| WO | WO2006138358 A2 | 12/2006 |
| WO | WO2006138358 A3 | 12/2006 |
| WO | WO2007042999 A2 | 4/2007 |
| WO | WO2007042999 A3 | 4/2007 |
| WO | WO2007089738 A2 | 8/2007 |
| WO | WO2007089738 A3 | 8/2007 |
| WO | WO2008011721 A1 | 1/2008 |
| WO | WO2008011721 A9 | 1/2008 |
| WO | WO2008038208 A2 | 4/2008 |
| WO | WO2008038208 A3 | 4/2008 |
| WO | WO2008038208 A8 | 4/2008 |
| WO | WO2008072125 | 6/2008 |
| WO | WO2008109298 A2 | 9/2008 |
| WO | WO2008109298 A3 | 9/2008 |
| WO | WO2009052423 | 4/2009 |
| WO | WO2009052425 | 4/2009 |
| WO | WO2010057095 A2 | 5/2010 |
| WO | WO2010057095 A3 | 5/2010 |
| WO | WO2011010257 | 1/2011 |
| WO | WO2011046665 | 4/2011 |

OTHER PUBLICATIONS

Kaplan, et al., "A Novel Fabrication Method of Capillary Tubes on Quartz for Chemical Analysis Applications," Industrial Microelectronics Center, PO Box 1084, S-164 21 Kista, Sweden, Fax +4687505430, Jan. 25-28. 1994. pp. 63-68.

Lin, et al., "Silicon Processed Microneedles" IEEE Journal of Microelectromechanical Systems. vol. 8 No. 1, Mar. 1999, 7 pages.

Seymour, John P., Kipke, Daryl R., "Neural probe design for reduced tissue encapsulation in CNS" Science Biomaterials 28 (2007) 3594-3607, Department of Biomedical Engineering, University of Michigan, 2212 Lurie Biomedical Engineering Building. 1101 Avenue, Ann Arbor, MI 48109-2099, USA, Mar. 27, 2007, 14 pages.

Seymour, et al., "The insulation performance of reactive parylene films in implantable electronic devices," Biomaterials 30 (2009) pp. 6158-6167, Aug. 22, 2009.

METHOD FOR IMPLANTING AN IMPLANTABLE DEVICE IN BODY TISSUE

CROSS-REFERENCE TO RELATED APPLICATIONS

The present application is a continuation application of Ser. No. 14/623,747, filed on Feb. 17, 2015, which is a continuation application of U.S. Pat. No. 8,958,862, issued on Feb. 17, 2015, which claims the benefit of U.S. Provisional Application No. 60/980,659, filed on Oct. 17, 2007, the disclosures of which are hereby incorporated in their entirety as if fully set forth below and for all applicable purposes.

This application is related to U.S. Pat. No. 8,731,673 which issued on May 20, 2014, which is incorporated in its entirety by this reference.

TECHNICAL FIELD

This invention relates generally to the implantable device field, and more specifically to an implantable device including a resorbable carrier.

BACKGROUND

Conventional microfabricated electrode arrays by themselves are often not mechanically robust enough to be inserted into body tissue. Therefore, they must be coupled to a carrier that is strong enough to resist buckling while being inserted into the tissue. Conventional carriers typically remain implanted with the microfabricated electrode arrays, potentially reducing the ability of the microfabricated electrode arrays to move freely in the tissue. Thus, there is a need for an improved carrier that increases the ability of the microfabricated electrode arrays to move freely. This invention provides such an improved and useful carrier.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1A:
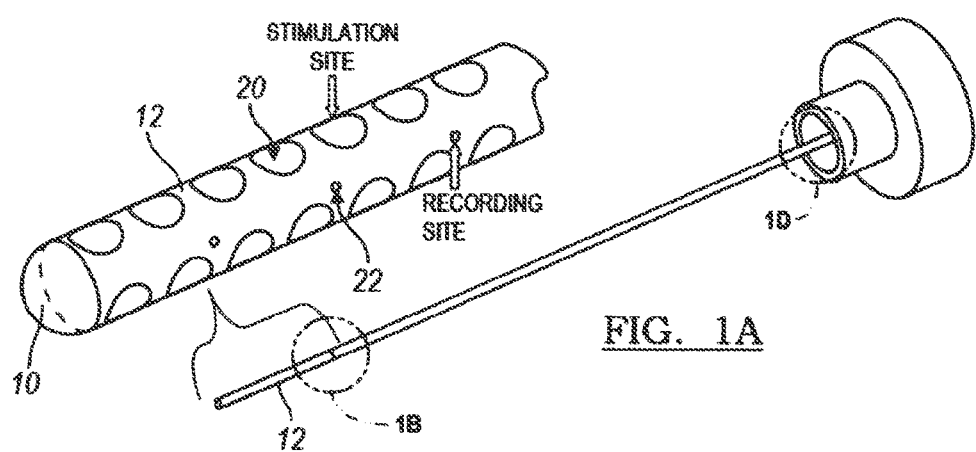
FIG. 1A is a representation of the device of the preferred embodiments of the invention.
Figure 1B:
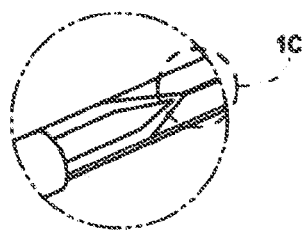
FIGS. 1B-1D are detailed views of FIG. 1A, showing a connector, a more detailed view of the connector, and a proximal end of the system, respectively.
Figure 1C:
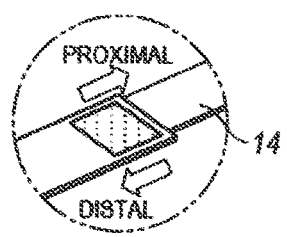
Figure 1D:
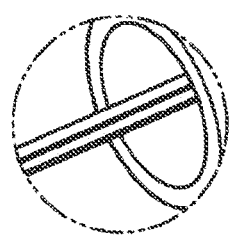
Figure 2:
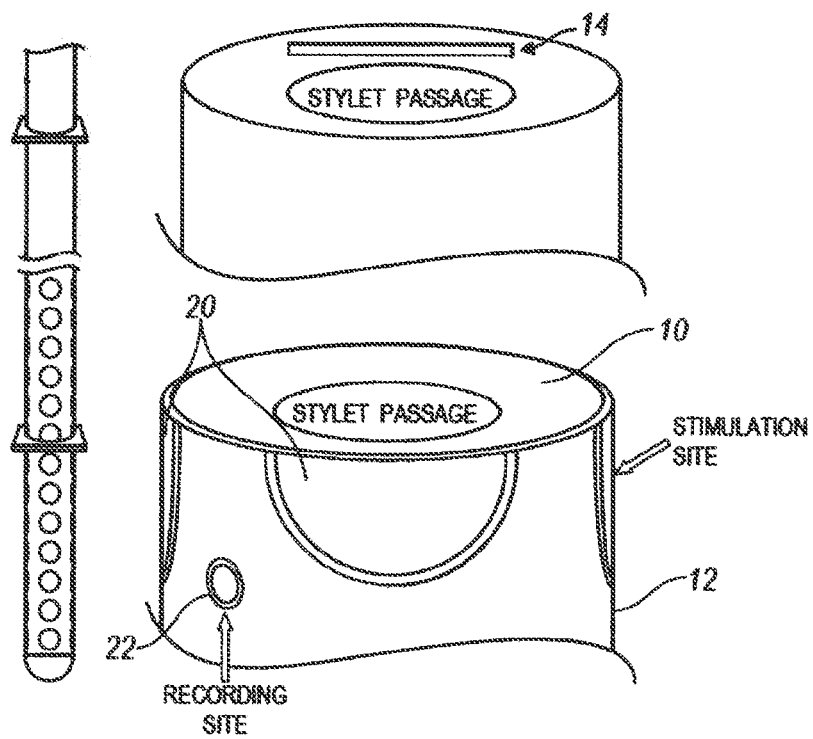
FIG. 2 is a representation of the device of FIG. 1, shown with two cross-sectional views.

As shown in FIGS. 1 and 2, the implantable device of the preferred embodiments includes a carrier 10 and an electrical subsystem 12 coupled to the carrier 10. The carrier 10 functions to facilitate the insertion of the electrical subsystem 12 and is adapted to allow the electrical subsystem 12 to move freely in the tissue. The implantable device is preferably designed to be implanted into the brain, spinal cord, peripheral nerve, muscle, or any other suitable anatomical location. The implantable device, however, may be alternatively used in any suitable environment and for any suitable reason.

The carrier 10 functions to facilitate the insertion of the electrical subsystem 12 and is adapted to allow the electrical subsystem 12 to move freely in the tissue or other substances. The electrical subsystem 12 is preferably attached to the carrier 10 such that the carrier functions to provide structural support. The carrier may include a sharpened end adapted to penetrate the tissue and aid in the insertion of the carrier and electrical subsystems into the tissue. The carrier 10 may also include alignment and or fixation features to facilitate positioning and stabilizing the electrical subsystem 12 in the tissue.

The carrier 10 of the preferred embodiments is resorbable into tissue after a period of time. Upon resorption of the carrier 10, the electrical subsystem 12 supported by the carrier will be left to float freely in the brain or other suitable tissue or material. The resorbable carrier is preferably made of a material that demonstrates at least one of the following characteristics: minimal foreign body reaction, biocompatibility, biodegradability, long-term mechanical and chemical stability, sterilizability, and sufficient porosity. The material is preferably adapted to undergo a controlled action and reaction to the surrounding tissue, a controlled chemical breakdown and resorption, replacement by regenerating tissue, stimulation of regeneration of living tissues, or any combination thereof. The resorbable carrier is preferably made from a bioresorbable polymer. The bioresorbable polymer is preferably polyglycolide or polylactide, but may alternatively be made from any suitable bioresorbable material such as a biodegradable magnesium alloy or a corrodible iron alloy. If the bioresorbable polymer is polyglycolide (or any other material that absorbs into the body after approximately one month), the carrier absorbs into the body at about the same time the body heals around the implanted device, which may be advantageous in some situations. If the bioresorbable polymer is polylactide (or any other material that absorbs into the body after approximately one year), the carrier absorbs into the body much after the body heals around the implanted device, which may be advantageous in other situations.

The carrier 10 may further extend the functionality of the device by providing fluidic channels through which therapeutic drugs, drugs to inhibit biologic response to the implant, or any other suitable fluid or substance may be transmitted. The fluidic channels are preferably channels defined by the geometry of the carrier 10, but may alternatively be separate microtubes molded, inserted, woven, knitted, or otherwise disposed into the carrier 10. The channels preferably provide for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener (or even a shape-memory alloy such as Nitinol) may be inserted to aid with the implantation or to facilitate post-implantation navigation of the device. The shape of the carrier is preferably tubular with about a 1-mm diameter, but may alternatively be solid or any other suitable shape of any suitable diameter for the desired functions.

The carrier 10 is preferably made from a material that is woven or knitted, but may alternative be made from a material that is cast, molded, or machined. The carrier 10 is preferably flexible, but may alternatively be rigid or semi rigid. The material may be uniformly rigid, or rigid only in a particular direction (such as the axial direction). The resorbable carrier may also be impregnated with fluids and/or deliver the fluids such as drugs and/or neurotrophins, similar to the "Stent Device and Method" of U.S. Pat. No. 7,001,680, which is incorporated in its entirety by this reference. The carrier 10 may be further adapted to act as a template for tissue regeneration and/or as a matrix for autologous or analogous cells or stem cells.

The carrier 10 may be made from a combination of materials. The layers or portions of distinct materials may have distinct absorption, degradation, or incorporation times. The distinct materials may further include distinct particles, agents, and/or cells that they deliver or release into the tissue. The carrier 10 may further include scaffolding for structural support and/or for drug or cell delivery. The scaffolding is preferably bioresorbable, but may alternatively remain implanted with the device.

The carrier 10 may be manufactured in one of several variations. In a first variation, the carrier may be manufactured such that the weave of the material is large enough to accept "weaving" of the electrical subsystem 12 directly into the fabric. In this variation, the electrical subsystem can be adapted to be woven in and out of the resorbable carrier to secure the electrical subsystem 12 to the carrier 10. A single electrical subsystem 12 could be woven into the fabric or multiple subsystems could be incorporated, resulting in a three-dimensional system of electrical subsystems. In a second variation, the electrical subsystem could be coupled directly to the surface of the carrier using a biocompatible adhesive such as epoxy or silicone. In this variation, the weave of the resorbable carrier may be tighter and/or the porosity of the carrier may be smaller as the electrical subsystem 12 is not woven into the material in this variation. In a third variation, the resorbable carrier may be manufactured as a concentric, multi-lumen structure. In this variation, the electrical subsystem 12 may be coupled to the carrier between the inner and outer lumens of the electrical subsystem.

Although the carrier 10 is preferably one of these several variations, of several various materials, manufactured in several variations, the carrier may be any suitable element, material, manufactured in any suitable fashion to facilitate the insertion of the electrical subsystem 12 and to allow the electrical subsystem 12 to move freely in the tissue or other substances.

The electrical subsystem 12 of the preferred embodiments functions to interface with the tissue, or any other suitable substance, within which it has been implanted. The electrical subsystem 12 may include multiple different electrical subsystems or a plurality of the same subsystems. The electrical subsystem 12 is preferably at least one of several versions or any combination thereof.

The electrical subsystem 12 is preferably a neural interface electrode array. The electrode array preferably has a plurality of electrode sites, and more preferably both stimulation sites 20 and recording sites 22. The neural interface electrode array is adapted to provide dynamic tunable electrical stimulation ranging from stimulation with macroscale specificity to microscale directional patterning. The electrode array is preferably adapted to optimally sample (record) and/or selectively activate (stimulate) neural populations. The plurality of electrode sites can be tuned for recording, stimulation, or any combination thereof. Additionally, at least two electrode sites may be grouped to form a larger composite site that enables tuning the neural interface region for recording and/or stimulation.

The neural interface electrode array is preferably made from a thin-film polymer substrate, such as parylene or some combination of parylene and inorganic dielectrics, but may alternatively be made out of any suitable material including, for example, silicon. The neural interface electrode array is preferably made such that there is high density of electrode sites at a first end of the array the distal end) and bonding regions at a second end of the array (the proximal end). The distal end of the array is preferably coupled to the carrier 10 to provide structural support. The electrode array may further include fluidic channels providing the capability to deliver therapeutic drugs, drugs to inhibit biologic response to the implant, or any other suitable fluid.

The neural interface electrode array in this variation is preferably a composite assembly that includes the neural interface electrode array and the carrier 10. The neural interface electrode array includes two pieces, a distal element and a proximal element. The distal element wraps or is woven around the circumference of the carrier 10. Ascending from the distal element, are preferably interconnects that transition from the outer surface of the carrier 10 into a single connector 14, such that the entire proximal element is imbedded in silicone. To facilitate adhesion between the carrier 10 and the neural interface electrode array, small non-homogeneous perforations are preferably micromachined in the neural interface electrode array to allow for the material of the carrier 10 to form a robust anchor with the electrode array.

Figure 3:
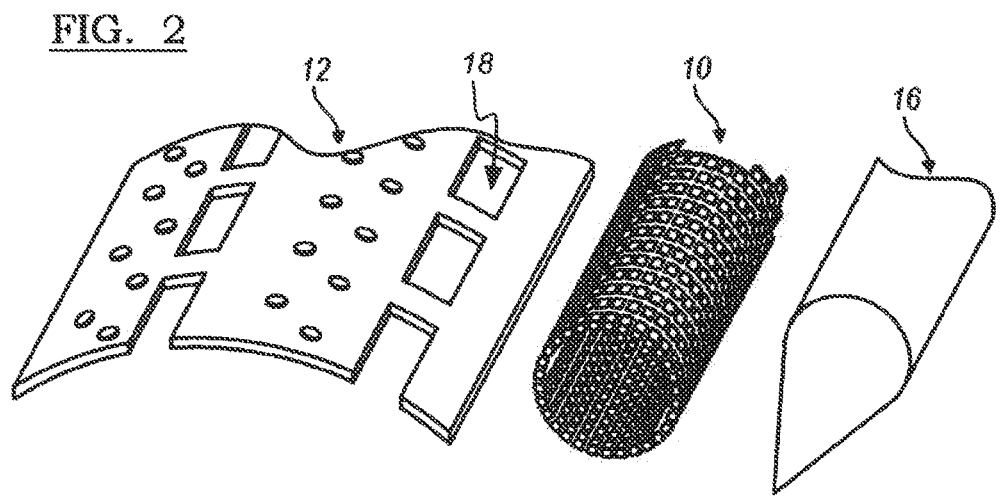
FIG. 3 is a representation of the device of a second version of the preferred embodiments of the invention, shown in an exploded, pre-assembled view.

In a second version of the preferred embodiments, as shown in FIG. 3, the neural interface electrode array preferably defines series of "cut-aways" or perforations 18 that axially extend in a discontinuous manner along the length of the neural interface electrode array. With the perforations, the neural interface electrode array preferably has adequate flexibility to allow bending and flowing of the device within body tissue after implantation of the device. The perforations 18 preferably extend in a radial direction completely through the neural interface electrode array, and preferably extend in a circumferential direction approximately 45-90 degrees. The neural interface electrode array preferably includes two perforation series, and thus the neural interface electrode array preferably extends 180-270 degrees in the areas with perforations. The perforation series is preferably discontinuous (i.e., the neural interface electrode array extends completely in the circumferential direction at particular points along the length of the neural interface electrode array). While the neural interface electrode array has been described as having perforations, it is also possible for the neural interface electrode array to be described as being one or more strips that are circumferentially connected by several "bridges".

In a third version of the preferred embodiments, the neural interface electrode array omits the "bridges" and is merely one or more rectangular and generally planar (i.e., either flat or slightly curved) "strips". The carrier provides structural support for these "strips" to be placed onto a stylet and implanted into body tissue. Although the electrical subsystem 12 is preferably one of these three versions, the electrical subsystem 12 may be any suitable element or combination of elements to perform the desired functions.

The device of the preferred embodiments may further include an additional electrical subsystem that functions to operate with the electrical subsystem 12. The additional electrical subsystem may include multiple different, electrical subsystems or a plurality of the same subsystems. The additional electrical subsystem is preferably at least one of several versions or any combination thereof. In a first version, the additional electrical subsystem is a suitable electronic subsystem to operate with an implantable neural interface. The additional electrical subsystem may be a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable pulse generator, an implantable rechargeable battery, integrated electronics for either real-time signal processing of the input (recorded) or output (stimulation) signals, integrated electronics for control of the fluidic components, any other suitable electrical subsystem, or any combination thereof. Although the additional electrical subsystem is preferably one of these several subsystems, the additional electrical subsystem may be any suitable element or combination of elements to operate any suitable electrical subsystem 12.

The device of the preferred embodiments may further include a connector 14 that functions to couple the electrical subsystem 12 to the additional electrical subsystem. The connector 14 is preferably one of several versions. As shown in FIGS. 1 and 2, the cable is preferably a flexible ribbon cable. The ribbon cable is preferably polymer ribbon cable, but may alternatively be any other suitable ribbon cable. The connector 14 may alternatively be any suitable element to couple the electrical subsystem 12 to the additional electrical subsystem, such as wires, conductive interconnects, etc. The ribbon cable may be encased in silicone or any other suitable material. In some versions, the electrical subsystem may have multiple ribbon cables. Preferably, multiple ribbon cables would be physically attached along their entire length, using a suitable adhesive such as medical grade adhesive or any other suitable connection mechanism. The cable is preferably connected to the electrical subsystems through ball bonds or any other suitable connection mechanisms. The connector 14 may alternatively be seamlessly manufactured with the first and or additional electrical subsystem. The connector 14 may further include fluidic channels adapted to deliver therapeutic drugs, drugs to inhibit biologic response to the implant, or any other suitable fluid.

As shown in FIG. 3, the device of the preferred embodiments may further include a stylet 16. The stylet 16 of the preferred embodiments functions to penetrate the tissue or other material and/or functions to provide structural support to the device during implantation of the device. The stylet 16 is preferably inserted into a lumen of the carrier 10, but may alternatively be located and inserted into any suitable component of the device in any suitable manner. The stylet 16 may include a sharpened end adapted to penetrate the tissue and aid in the insertion of the stylet, the carrier 10, and/or the electrical subsystems into the tissue. The stylet 16 is preferably removed from the tissue following the placement of an electrical subsystem, but may alternatively be adapted to remain in the tissue while still allowing the implanted electrical subsystem 12 to float freely in the brain. This may be accomplished by the stylet being selectively flexible (through electrical stimulus or other suitable method) or by being resorbable into the tissue after a period of time. The stylet 16 is preferably made from a stiff material such as metal, but may alternatively be made from any suitable material. In one variation, the metal is an insulated metal wire. In this variation, the insulated metal wire may not have insulation covering a sharpened tip, and thus can be used as a conventional single-channel microelectrode.

Figure 4A:
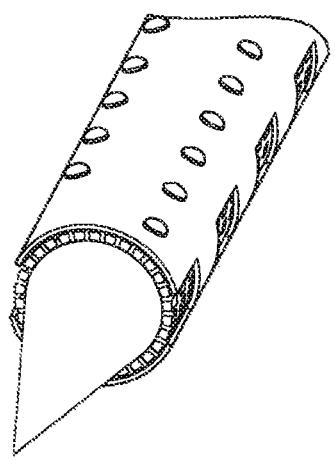
FIG. 4A-C are representations of the method of the preferred embodiments of the invention, shown with the three major steps.
Figure 4B:
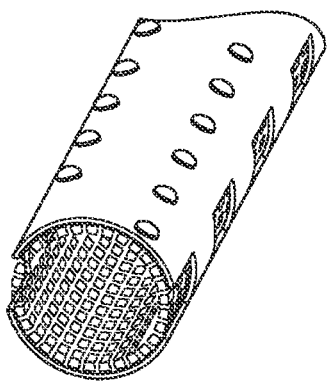
Figure 4C:
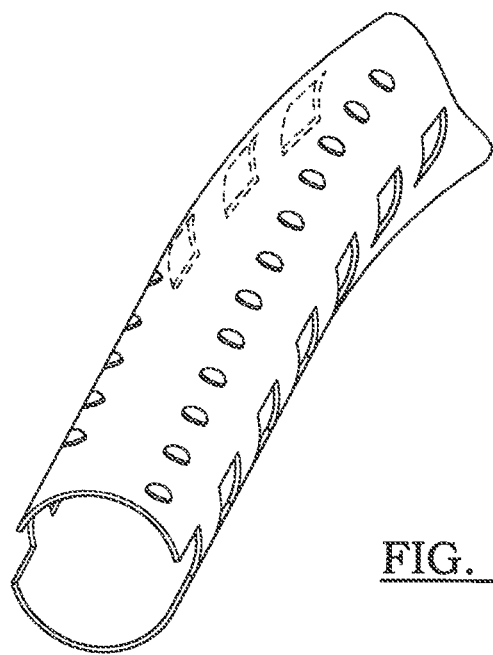

As shown in FIG. 4, a method of implanting and using the implantable device and its corresponding electrical components preferably includes the following steps: (a) providing an electrical subsystem and a carrier that provides structural support for the electrical subsystem; (b) implanting the electrical subsystem and the carrier into the body tissue; and (c) dissolving the carrier into the body tissue and allowing the electrical subsystem to flex within and interface with the body tissue. Step (c) may include dissolving the carrier into the body tissue at a rate approximately equal to the healing process of the body tissue, or may include dissolving the carrier into the body tissue at a rate much slower than the healing process of the body tissue. The method may also include providing a stylet, placing the electrical subsystem and the carrier onto the stylet, and penetrating the body tissue with the stylet.

Although omitted for conciseness, the preferred embodiments include every combination and permutation of the various carriers 10, the various electrical subsystems, the various connectors, the various stylets, and the various methods of use. As a person skilled in the art will recognize from the previous detailed description and from the figures and claims, modifications and changes can be made to the preferred embodiments of the invention without departing from the scope of this invention defined in the following claim.

What is claimed is:

1. A method for assembling a neural interface device, comprising:

providing a carrier extending along a first carrier length from a proximal carrier portion to a distal carrier portion having a distal carrier end, wherein the carrier is of a bioresorbable material such that the carrier is absorbable into body tissue at a time that occurs after implantation of the neural interface device into body tissue;

providing a first electrical subsystem that includes a plurality of electrode sites and an electrode substrate that has a tubular shape and that supports the plurality of electrode sites; and weaving at least a portion of the electrode substrate with the carrier to form the neural interface device so that the plurality of electrode sites extends circumferentially relative to the first carrier length of the carrier and has exposed surfaces facing outwardly from the electrode substrate opposite the carrier.

2. The method of claim 1, further comprising:

providing a stylet adapted to penetrate the body tissue; and supporting the neural interface device on the stylet.

3. The method of claim 1, including providing the first electrical subsystem being flexible after absorption of the carrier into the body tissue.

4. The method of claim 1, including selecting the bioresorbable material of the carrier from a group consisting of polyglycolide, polylactide, a magnesium alloy, and a corrodible iron alloy.

5. The method of claim 1, including providing the carrier having a tubular shape.

6. The method of claim 5, including providing the tubular carrier having a diameter of about one millimeter.

7. The method of claim 1, including providing the carrier having a woven structure that enables the at least the portion of the electrical substrate to be woven into the carrier.

8. The method of claim 1, including providing the first electrical subsystem having a plurality of electrode sites that are configured to electrically stimulate different portions of neural tissue.

9. The method of claim 1, including providing the plurality of electrode sites supported by the electrode substrate so that the electrode sites extend both circumferentially and axially relative to the first carrier length.

10. The method of claim 1, including providing a plurality of electrode sites supported by the electrode substrate, and configuring the electrode sites to electrically record from different portions of neural tissue.

11. The method of claim 1, including providing the electrode substrate being of a thin-film polymer selected from a group consisting of parylene and silicone.

12. The method of claim 1, including providing the electrode substrate having a series of perforations that extend axially in a discontinuous manner along a second electrode substrate length.

13. The method of claim 1, including providing the first electrical subsystem having an elongated, substantially planar shape.

14. The method of claim 1, including providing an electrical connector extending from each of the plurality of electrode sites to a proximal connector portion adjacent to the proximal carrier portion.

15. The method of claim 14, including electrically connecting the proximal connector portion of the first electrical subsystem to a second electrical subsystem that is configured to control at least one electrode site.

16. The method of claim 1, including providing a lumen extending through the carrier from the proximal carrier portion to the distal carrier end.

17. The method of claim 1, including providing the electrode substrate comprising longitudinal and circumferential bridge strips, wherein at least two longitudinal bridge strips are connected by at least three lateral bridge strips, thereby defining a series of discontinuous perforations in the electrode substrate of the first electrical subsystem.

18. The method of claim 1, including providing the carrier comprising an inner tubular sidewall disposed inside an outer tubular sidewall with the first electrical subsystem located between the inner and outer tubular sidewalls, but with the exposed surface of at least one electrode site facing outwardly from the electrode substrate opposite the inner and outer tubular sidewalls.

19. A method for assembling a neural interface device, comprising:
   forming a carrier having a woven structure and a tubular shape from a bioresorbable material that is absorbable into body tissue after implantation, wherein the woven structure has a sufficiently large weave to allow an electrical subsystem to be woven into the carrier; and
   weaving at least a portion of an electrode substrate of the electrical subsystem with the carrier to form the neural interface device so that a plurality of electrode sites supported by the electrode substrate are disposed circumferentially and axially relative to a first carrier length of the carrier and have exposed surfaces facing outwardly from the electrode substrate opposite the carrier.

20. The method of claim 19, wherein the bioresorbable material comprises at least one of a polyglycolide, polylactide, a magnesium alloy, or a corrodible iron alloy.

* * * * *